United States Patent [19]

Kelley et al.

[11] 4,299,794
[45] Nov. 10, 1981

[54] ANALYTICAL SYSTEM FOR ANALYZING $CO_2$ CONTENT OF A FLUID

[75] Inventors: Thomas F. Kelley, Canton; Dinesh I. Mody, Bedford; Charles F. Mountain, Cambridge, all of Mass.

[73] Assignee: Instrumentation Laboratory Inc., Lexington, Mass.

[21] Appl. No.: 161,375

[22] Filed: Jun. 20, 1980

[51] Int. Cl.[3] .................... G01N 33/50; G01N 1/10; G01N 7/14
[52] U.S. Cl. .................... 422/68; 23/230 B; 23/232 R; 422/81; 422/83; 422/103
[58] Field of Search .................... 422/50, 68, 81, 103, 422/83; 23/230 B, 232 R; 128/635; 73/421 R, 421.5 R; 364/497, 558

[56] References Cited

U.S. PATENT DOCUMENTS

| | | | |
|---|---|---|---|
| 3,068,855 | 12/1962 | Furlong, Jr. | 422/68 |
| 3,222,135 | 12/1965 | Ashmead . | |
| 3,756,782 | 9/1973 | Phillips | 23/230 B |
| 3,763,422 | 10/1973 | MacPhee et al. | 422/68 X |
| 4,019,861 | 4/1977 | Dahms | 422/68 X |
| 4,197,853 | 4/1980 | Parker | 128/635 |

OTHER PUBLICATIONS

IL 445 Chloride/TCO2 Analyzer–Operators Manual (1977), Instrumentation Laboratory, Inc., 113 Hartwell Ave., Lexington, MA 02173.
Peters et al., Quantitative Clinical Chem., vol. II, pp. 229-262b, Williams & Wilkins Co., Balt., Md., 1932.

Primary Examiner—Ronald Serwin

[57] ABSTRACT

A total carbon dioxide analyzer system has a reaction chamber that includes a tube and a piston mounted for sliding movement in the tube to change the volume of the chamber. A valve coupled to the chamber has a sample inlet port and a reagent inlet port, and is movable between a first state in which the sample inlet port is connected to the chamber, a second state in which the reagent inlet port is connected to the chamber, and a third state in which the reaction chamber is sealed. A system controller coordinately operates the valve and moves the piston to increase the volume of said chamber to draw sample into the chamber for mixing with an acid reagent in the chamber, and then seals the chamber and increases the volume of the chamber to facilitate the release of carbon dioxide. A transducer then senses the pressure of carbon dioxide in the reaction chamber.

15 Claims, 12 Drawing Figures

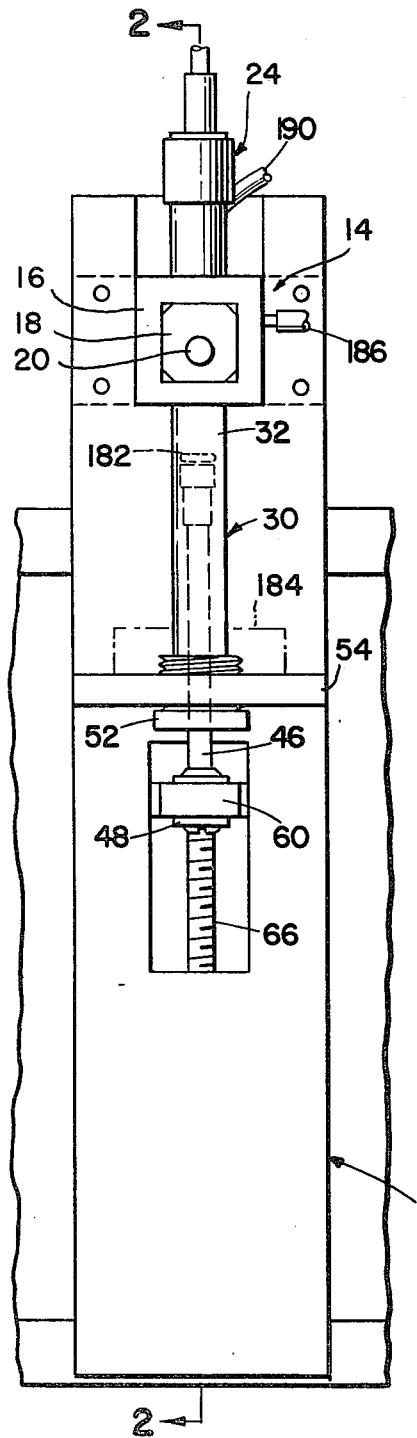
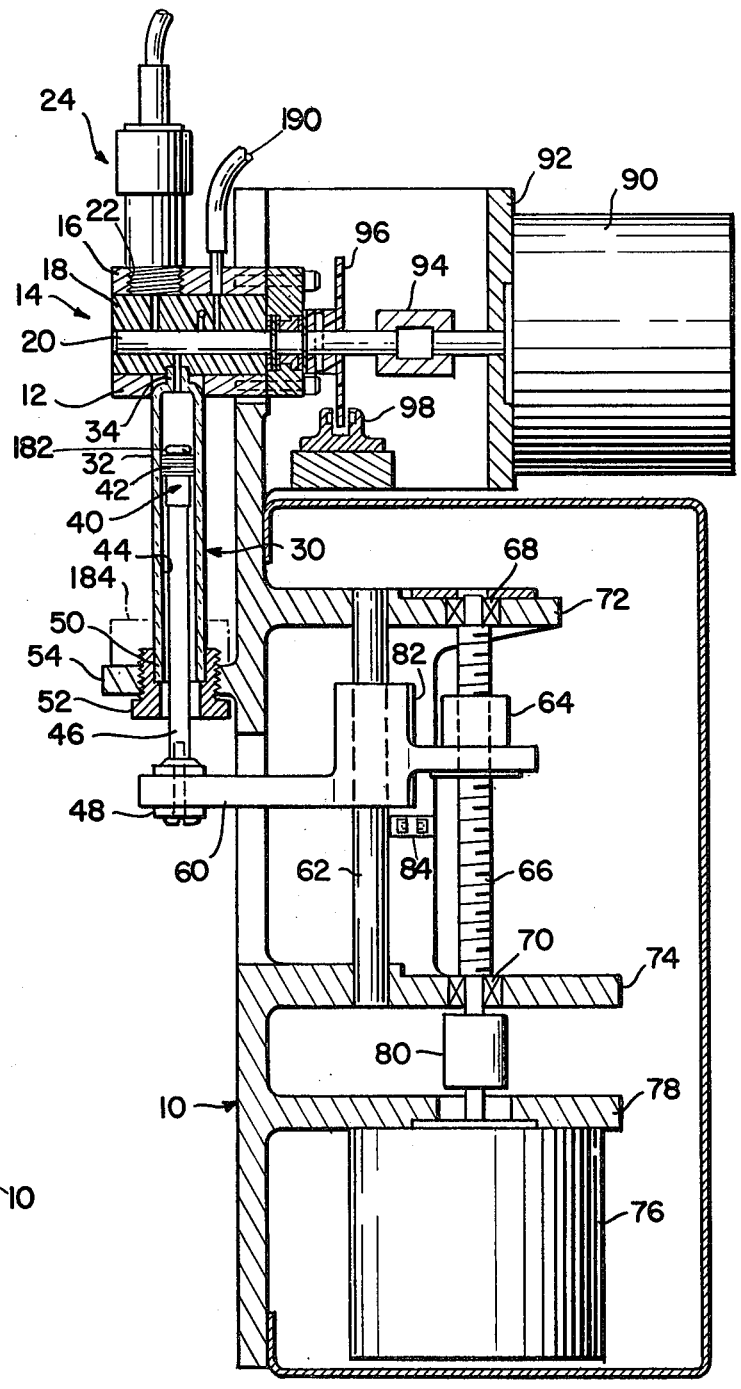
Fig. 1
Fig. 2

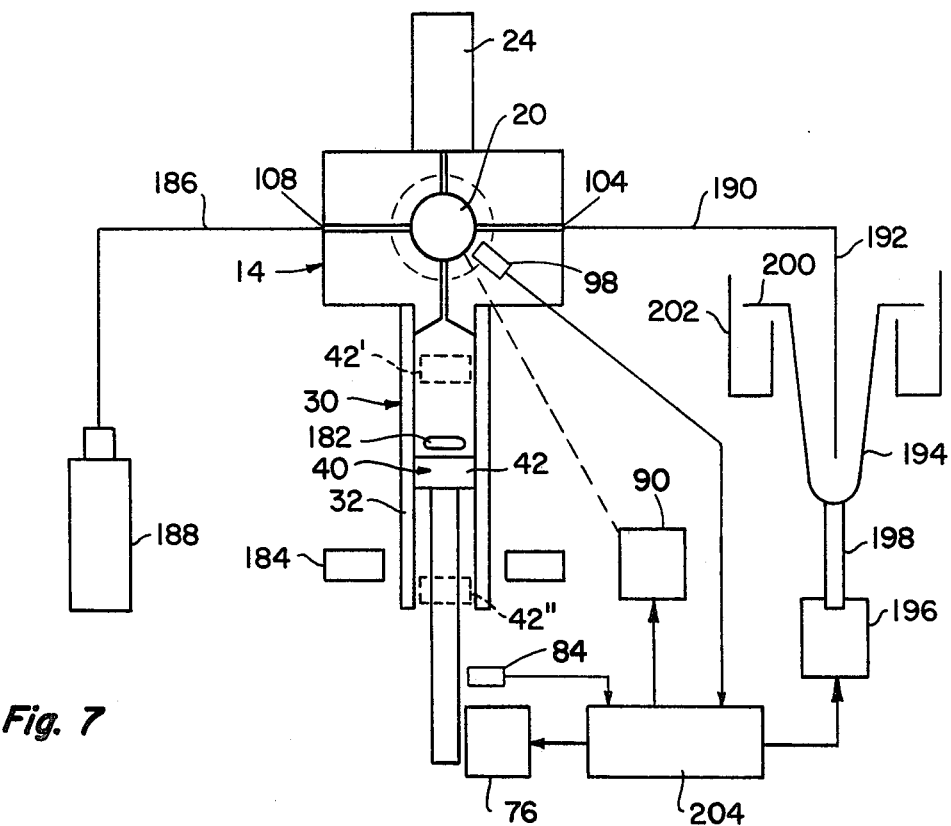
Fig. 7
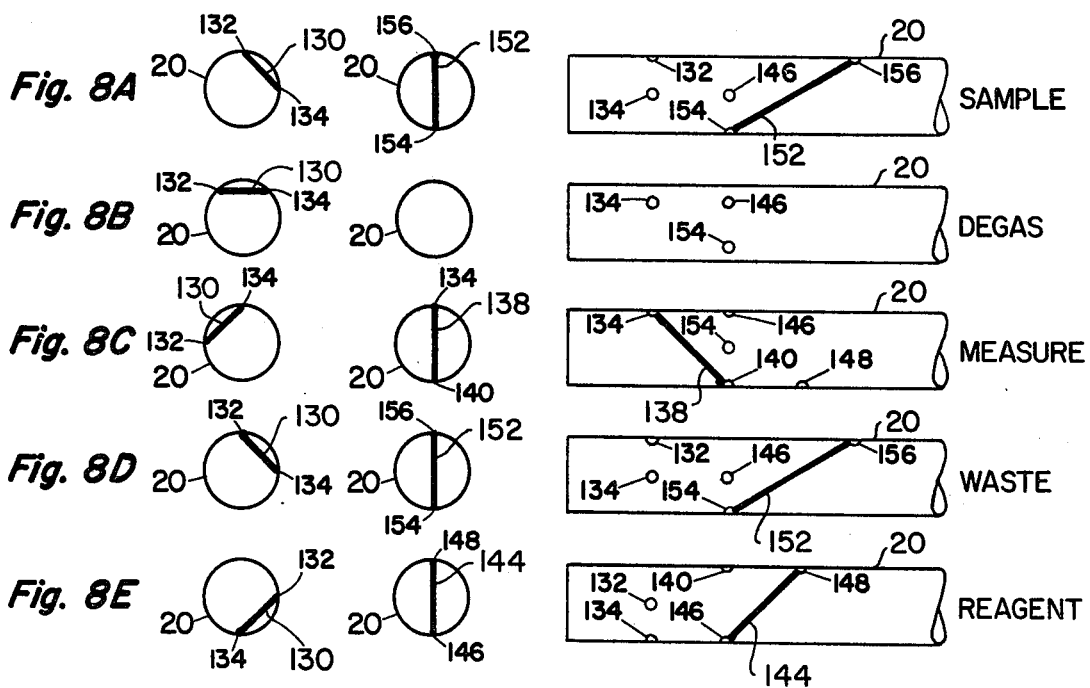

ANALYTICAL SYSTEM FOR ANALYZING CO₂ CONTENT OF A FLUID

This invention relates to analytical systems and processes and more particularly to systems and processes for the measurement of carbon dioxide in fluids.

Carbon dioxide (in combined form and in dissolved form) is present in a wide range of fluids including natural waters, precious fluids such as plasma and serum, and excretory fluids such as urine. Carbon dioxide, being one of the main products of cell metabolism and constantly being formed in the cell organisms, is always available in the environment and inside cells. The bicarbonate buffer system is a main buffer system of cells and of plasma and of body fluids of living organisms. As such, the carbon dioxide content of such fluids will frequently provide useful diagnostic or analytical information.

In serum and plasma, for example, the total carbon dioxide content includes bicarbonate, carbonic acid, and dissolved and protein-bound carbon dioxide, and may be expressed:

$$TCO_2 = HCO_3^- + H_2CO_3 + CO_2$$

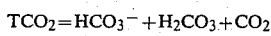

Total carbon dioxide ($TCO_2$), when considered with other sources of acid-base information such as pH, may be differentiated, through calculation, into its $HCO_3^-$ and $H_2CO_3$ components. Commonly, $TCO_2$ is used semiquantitatively with clinical signs or other electrolyte values, particularly potassium and chloride levels, to provide insight into the nature of metabolic disturbances, the effectiveness of therapeutic measures, and to assist in the control of life support devices. $TCO_2$ in venous serum and plasma normally ranges from 23 to 30 mmol/l.

A number of different techniques have been employed to measure carbon dioxide content of fluids. The VanSlyke method, for example, involves the manual manipulation of a mercury column—an awkward and time consuming process. Other techniques that have been employed, including electrochemical electrode systems of the $PCO_2$ type, differential pH systems, and infrared photometry systems, have limitations such as frequent calibration requirements, membrane maintenance problems, requirements of large sample size, and slow throughput.

In accordance with the invention there is provided an analytical system that includes a variable volume reaction chamber with a valved inlet. Both the volume of the chamber and the condition of the valve are adjusted in coordinated manner by a system controller, and when the valve is open, liquids are flowed into and out of the reaction chamber by change of chamber volume. In operation, a sample to be analyzed and an acid reactant (that interacts with the sample to produce carbon dioxide) are flowed into the chamber by increase in chamber volume, and the controller then seals the chamber by closing the valve. Carbon dioxide is then generated:

$$CO_3^= + HCO_3^- + nH^+ \rightleftharpoons H_2CO_3 \rightleftharpoons CO_2 + H_2O.$$

The volume of the sealed chamber is increased (reducing the pressure) and the mixture is stirred to enhance the release of dissolved carbon dioxide into the gaseous phase, and then the quantity of carbon dioxide in the chamber is measured. While various carbon dioxide sensing techniques may be utilized, including infrared photometry and hot wire anemometer techniques, a pressure transducer type of sensor is used in preferred embodiments. Preferably, the pressure transducer is connected to the reaction chamber by the valve after the degassing interval and the chamber volume has been reduced to a predetermined value (so that the pressure is less than ambient pressure and within the measurement range of the transducer). In the particular embodiment of the transducer is of the piezoelectric type and measures a range of 0 to 60 mmCO₂/liter (a pressure range of about 6-11 psia). This measurement under reduced pressure prevents the appearance of physical water in the transducer chamber. It will be apparent that other pressure dependent measurement arrangements such as the measurement of carbon dioxide as a function of the volume of the reaction chamber at a predetermined pressure may be used.

While the invention is useful in measuring carbon dioxide content of many different fluids, including industrial wastes and industrial process fluids, in a particular embodiment total carbon dioxide in serum and plasma is determined in a system that utilizes a sample volume of less than fifty microliters. The reaction chamber includes a cylinder and piston arrangement, in which axial displacement of the piston changes the volume of the reaction chamber. A compact minimum "deadspace" valve arrangement mounted on the chamber cylinder has separate inlets for the acid reagent and for the diluted sample. The valve includes a seal block of plastic material with lateral porting from a bore in which a movable valve member is press fitted. The valve member has a plurality of through passages, each of which has a volume of less than twenty microliters. A stirring mechanism in the chamber is driven by an external electromagnetic actuator for enhancing release of carbon dioxide from the liquid. While a variety of acid reagents may be utilized, in this embodiment the acid reagent is lactic acid of sufficient strength to cause the final reaction mixture (diluted sample and reagent) to have a pH of less than 3.0. The lactic acid used interacts with the bicarbonate in the sample to produce carbon dioxide but does not precipitate the protein constituents of the sample. The acid reagent is also used for cleaning and is flushed through the line through which the sample is introduced in system cleaning sequence.

The invention provides accurate analysis of carbon dioxide content of fluids in an analysis cycle of short duration and in an easily automated arrangement.

Other features and advantages of the invention will be seen as the following description of a particular embodiment progresses, in conjunction with the drawings in which:

FIG. 1 is a front elevational view of analysis apparatus in accordance with the invention;

FIG. 2 is a sectional view taken along the line 2—2 of FIG. 1;

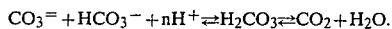

Figure 5:
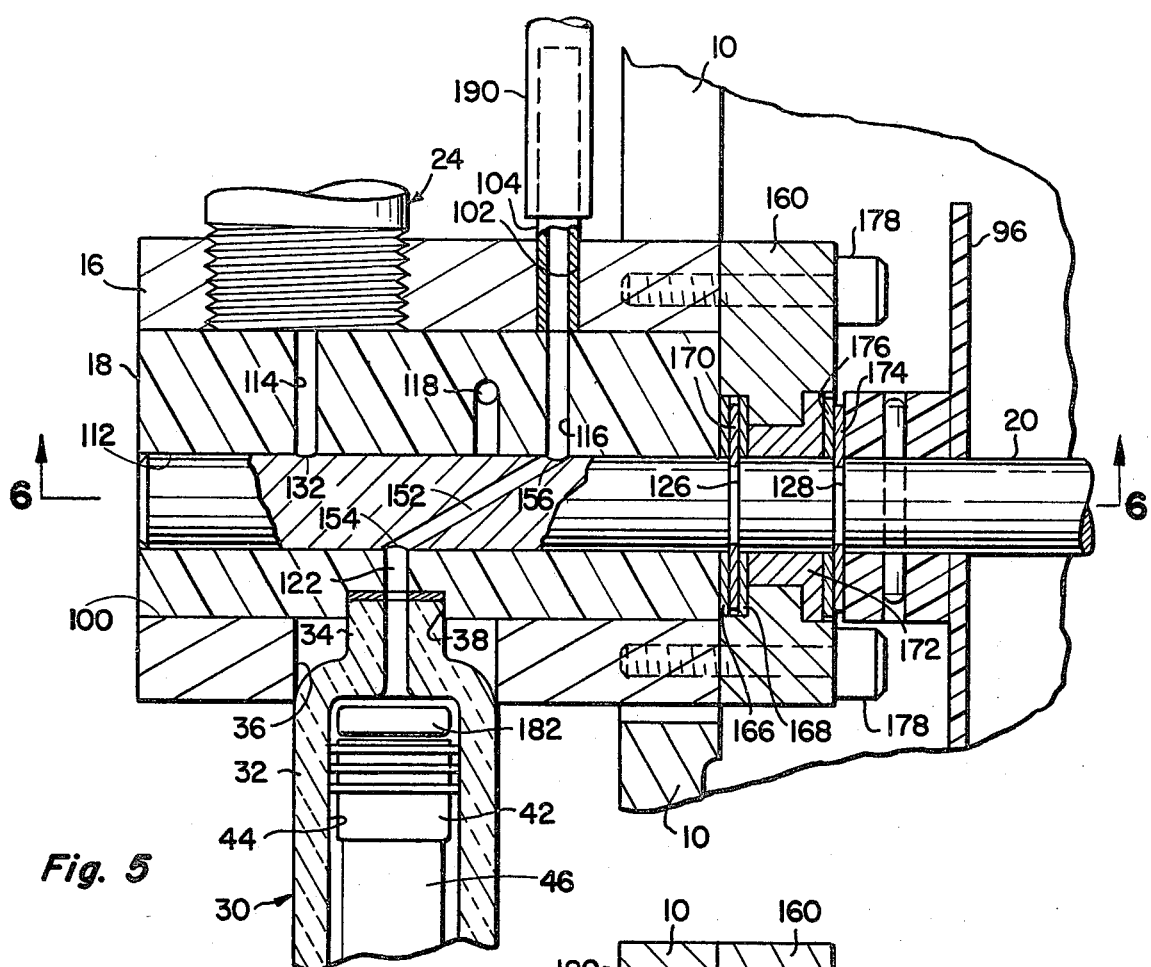

FIG. 5 is an enlarged sectional view of the valve shown in FIG. 2.

Figure 6:
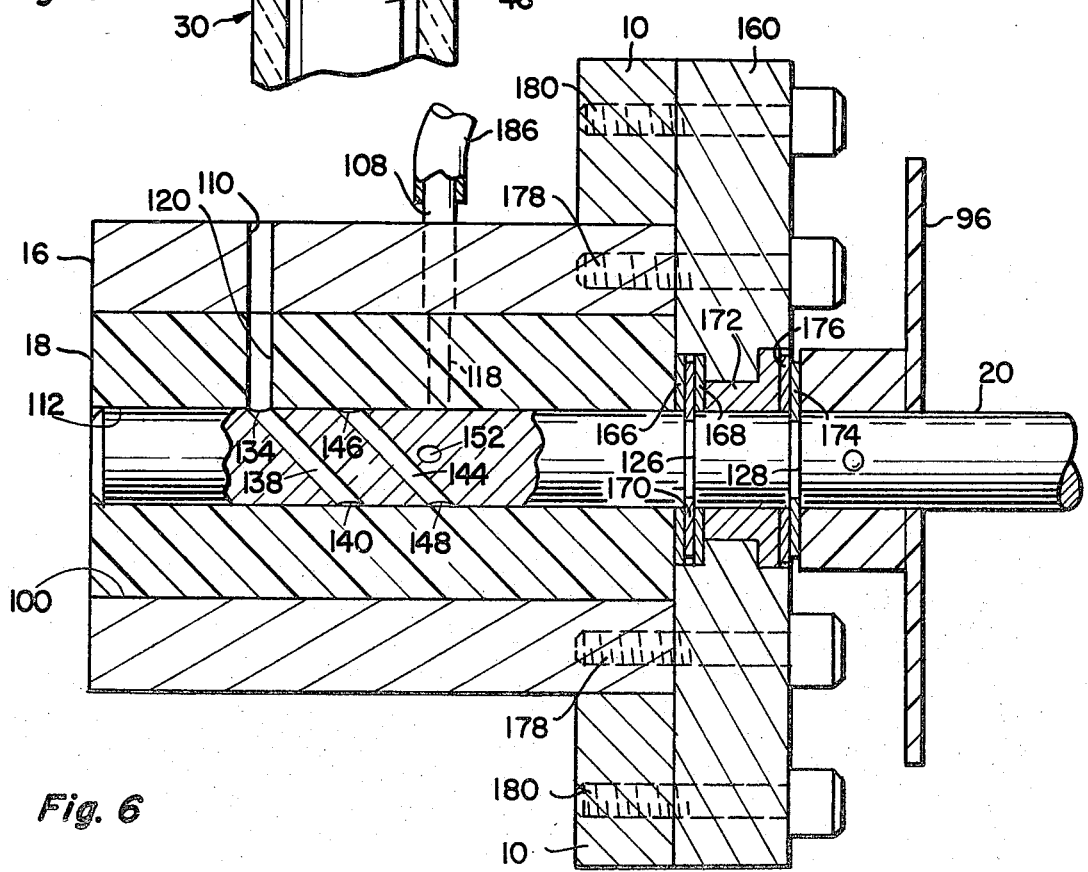

FIG. 6 is a sectional view taken along the line 6—6 of FIG. 5;

FIG. 7 is a diagrammatic view of an analysis system including the apparatus shown in FIG. 1; and FIG. 8 is a set of diagrams showing a series of valve positions during operation of the system of FIG. 7.

DESCRIPTION OF PARTICULAR EMBODIMENT

There is shown in FIGS. 1 and 2 apparatus for measuring the carbon dioxide content of a fluid sample such as blood serum or urine. The apparatus includes a frame member 10 on which a valve assembly 14 is mounted. That valve assembly includes a housing member 16, a seal member 18, and a shaft member 20. Pressure transducer 24 is threadedly received in port 22 and projects from the upper surface of housing 16.

A variable volume reaction chamber 30 is disposed below valve assembly 14 and includes a cylindrical glass tube 32, the upper end 34 of which is of reduced diameter and extends through aperture 36 and is seated in a recess 38 in seal member 18. Disposed within tube 32 is a piston assembly 40 that includes a head portion 42 in sealing engagement with the inner surface 44 of tube 32, a shaft portion 46 and a coupling portion 48. The lower end 50 of tube 32 is seated on support member 52 which is threaded in support flange 54 and adjusted such that the upper end 34 of tube 32 is firmly seated against seal member 18.

A controller mechanism connected to piston coupling 48 includes coupling member 60 that is mounted for vertical movement along guide rod 62 and that carries nut 64 in engagement with lead screw 66. Bearing assemblies 68, 70 in frame flanges 72, 74 support lead screw 66 for rotation, and stepping motor 76 (mounted on flange 78) drives lead screw 66 through coupling 80. A piston position indicator assembly includes tab 82 mounted for movement with coupling member 60, and cooperating sensor assembly 84 mounted on frame 10.

The position of shaft 20 of valve assembly 14 is controlled by stepper motor 90 which is supported on bracket 92 and connected to shaft 20 by means of coupling 94. A valve shaft position indicator assembly includes disc 96 and sensor assembly 98.

Figure 3:
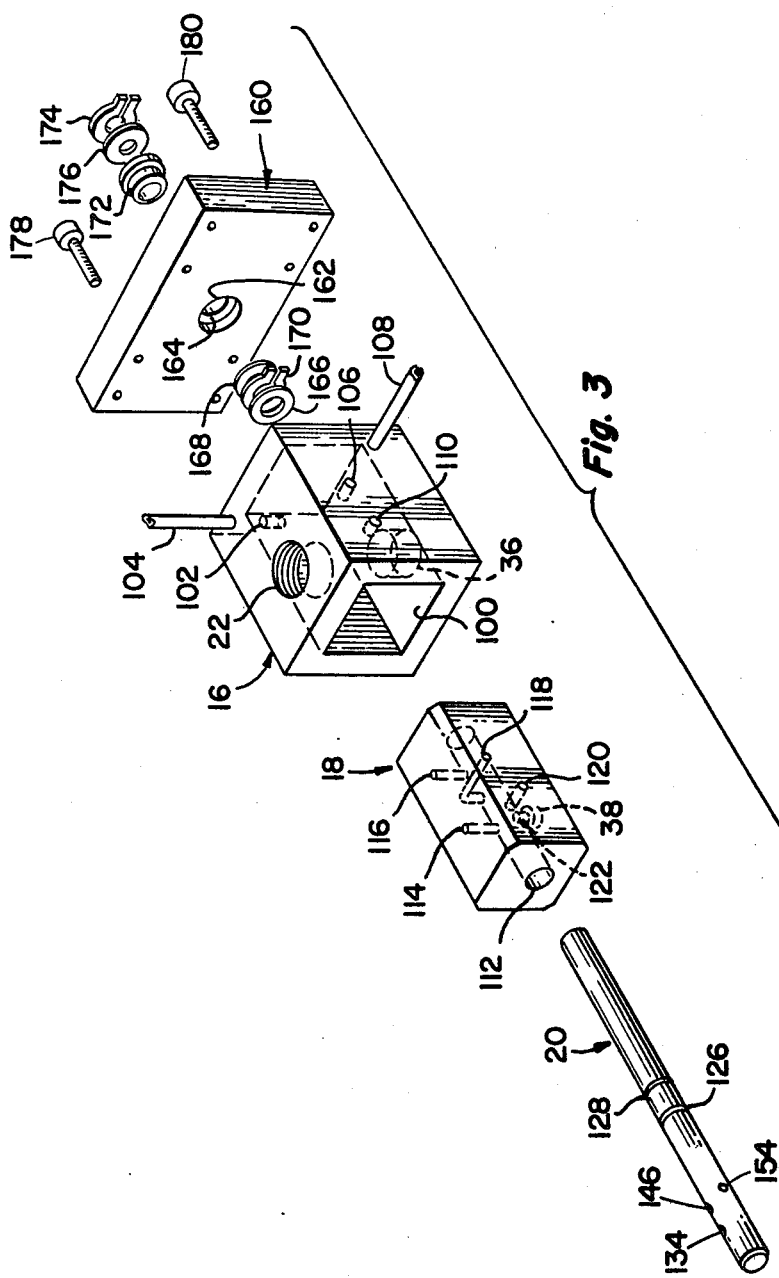
FIG. 3 is an exploded perspective view of components of the valve employed in the analysis system of FIGS. 1 and 2.

Further details of valve assembly 14 may be seen with reference to the exploded view of FIG. 3. Valve housing 16 is an aluminum member that defines a rectangular through passage 100 that is about two centimeters on each side and about three centimeters in length. Formed in the upper wall of housing 16 (to the rear of transducer port 22) is through bore 102 that receives sample inlet coupling tube 104. Formed in a side wall of housing 16 (forward of bore 102) are a through bore 106 that receives reagent inlet coupling tube 108, and (forward of bore 106) a vent port 110. Aperture 36 in the bottom wall of housing 16 receives the upper end of reaction chamber tube 32.

Seal member 18 (of tetrafluoroethylene—Teflon) is received within rectangular through passage 100 of valve housing 16. The rectangular dimensions of seal member 18 are slightly greater (about 0.05 millimeter) than the rectangular dimensions of passage 100. Seal member 18 has a cylindrical through passage 112 about 0.6 centimeter in diameter, and an array of five passages, each about 1½ millimeter in diameter, that extend radially from through passage 112: transducer passage 114 and sample passage 116 each extend upwardly to the upper surface of seal member 18; reagent passage 118 extends radially upwardly from through passage 112 and then transversely to a side wall of seal member 18; vent passage 120 extends radially to the same side wall; and reaction chamber passage 122 extends downwardly from through passage 112 to a coaxial recess 38 in which the upper end 34 of reaction tube 32 is seated.

Figure 4:
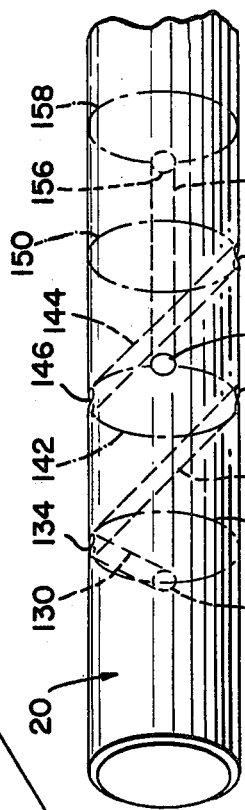
FIG. 4 is a perspective view of a portion of the valve shaft showing its porting.

Stainless steel shaft 20 is received within passage 112 of seal member 18 and has a diameter about 0.1 millimeter greater than that of bore 112. Shaft 20 has two annular grooves 126, 128; and four passages, each about one millimeter in diameter, are drilled through the shaft. As indicated in FIG. 4, a first passage 130 extends between ports 132 and 134 that are located in the same radial plane 136 and spaced 90 degrees apart; a second passage 138 extends between port 134 and port 140 which is in a second radial plane 142 axially spaced from plane 136; a third passage 144 extends from a port 146 (located 180 degrees from port 140 in radial plane 142) to a port 148 in radial plane 150; and passage 152 extends from port 154 (located in radial plane 142 and offset 90 degrees from ports 140 and 146) to port 156 in radial plane 158. Each of passages 138, 144 and 152 extends through shaft 20 from one side to the other, that is the two ports of each passage are on opposite sides of the shaft. When shaft 20 is positioned within seal block 18, radial plane 136 is aligned with transducer passage 114, radial plane 142 is aligned with chamber passage 122, radial plane 150 is aligned with reagent passage 118, and radial plane 158 is aligned with sample passage 116.

Mounting plate 160 has a bore 162 through which shaft 20 extends; a coaxial recess 164 in its front face that receives an assembly of washers 166, 168 and snap ring 170 that is seated in annular groove 126; and a coaxial recess in its rear face which receives bushing 172. Snap ring 174 is seated in annular groove 128 and washer 176 spaces bushing 172 from snap ring 174.

Further details of the valve assembly and associated components may be seen with reference to FIGS. 5 and 6. As there indicated bolts 178 secure valve housing 16 to mounting plate 160, and bolts 180 secure mounting plate 160 to frame 10.

As shown in FIG. 5, housed in reaction chamber 30 on piston head 42 is magnetic stir bar 182 that is rotated by the electromagnetic drive mechanism 184 that is supported on flange 54 as indicated in FIGS. 1 and 2 when piston head 42 is in its bottom position 42".

A diagrammatic representation of the analysis system is shown in FIG. 7. Valve 14 is mounted on top of the variable volume reaction chamber 30 and transducer 24 is mounted on top of valve 14. Connected to reagent inlet 108 via line 186 is a supply 188 of reagent which, in this embodiment, is one M lactic acid. Connected to sample inlet 104 via line 190 and probe 192 is a spin cup 194 that is driven in rotation (bidirectionally) by motor 196 and shaft 198. Spin cup is of conical shape and has at its upper end an annular lip 200 which overlies annular waste chamber 202. Motor 196 is controlled by system controller 204 (which is a microprocessor in a preferred embodiment) to rotate spin cup 194 briefly in opposite directions to achieve thorough mixing of sample and diluent; and to rotate cup 194 at high speed to expel its contents over lip 200 into waste chamber 202. System controller 204 also controls valve stepper motor 90 and piston stepper motor 76.

Sample line 190 (including probe 192) has a volume of about 190 microliters and the volume of reaction chamber 30 is varied by axial movement of piston 40. Piston head 42 moves between an upper position 42' in which the chamber volume is about 300 microliters and a lower position 42" in which the chamber volume is about 4200 microliters and spin bar 182 is positioned within the electromagnetic drive 184. Axial movement of piston 40 is controlled by stepper motor 76 which drives lead screw 66, and sensor assembly 82, 84 indicates an axial index position of piston head 42.

Valve 14 is controlled by stepper motor 90 with an angular index position being indicated by sensor assembly 96, 98, and is indexed between a "sample" position (FIG. 8A), a "seal" position (FIG. 8B), a "sensor" position (FIG. 8C), a "discharge" position (FIG. 8D) which is the same as the FIG. 8A sample position, and a "reagent" position (FIG. 8E). In the "reagent" position, shaft port 146 is aligned with seal passage 122 so that reagent passage 118 and chamber passage 122 in seal member 18 are connected by shaft passage 144. Rotation of the shaft 90 degrees to the FIG. 8A position also (shown in FIG. 5) aligns shaft port 154 with seal passage 122 so that chamber passage 122 and sample passage 116 are connected by shaft passage 152. In this valve position, (as indicated in FIGS. 5 and 6) shaft passage 130 connects transducer passage 114 with vent passage 120 so that the transducer 24 is exposed to ambient pressure for equilibration. Indexing of the shaft 45 degrees to the FIG. 8B position places the system in a "degassing" mode in which reaction chamber 30 is sealed. Indexing of the shaft 45 degrees further (to the FIG. 8C position) aligns shaft port 140 with chamber passage 122 so that shaft passage 138 connects reaction chamber 30 and transducer 24 and the system is in a "measuring" mode.

In system operation, operation of motors 76, 90 and 196 are coordinated by system controller 204 to provide sequential analysis cycles. With reagent in the reaction chamber, piston 40 in its upper position 42', and valve 14 initially in the position shown in FIG. 8A, a sample of the material to be analyzed (serum or urine) and a buffered diluent (at a sample:diluent ratio of about 1:7) are placed in spin cup 194 and mixed by bidirectional rotation of cup 194 under the control of system controller 204. Controller 204 then operates stepper motor 76 to rotate lead screw 66 and drive piston 40 downwardly to increase the volume of reaction chamber 30 about four hundred microliters. This operation first flows reagent from line 190 into chamber 30 followed by about two hundred ten microliters of the diluted sample from sample cup 194.

Controller 204 then rotates valve shaft 20 45 degrees to the "degassing" position indicated in FIG. 8B in which reaction chamber 30 is sealed. After chamber 30 is sealed, controller 204 operates stepper motor 76 to drive piston 40 downwardly to the position 42" in which stir bar 182 is positioned in the electromagnetic drive field of the stir bar drive mechanism 184 and the volume of the reaction chamber is about 4200 microliters (a gas volume of about 3500 microliters). Stir bar 182 spins rapidly to mix the diluted sample and reagent and the bicarbonate reaction produces carbon dioxide from its combined forms which, together with dissolved $CO_2$, is released in this reduced pressure environment. After a "degassing" interval of about seven seconds under reduced pressure in the reaction chamber 30, controller 204 operates stepper motor 76 to raise piston 42 to the position shown in FIG. 7 to provide a gas volume of about 150 microliters above the degassed liquid sample. Stepper motor 90 is then operated to rotate the valve shaft 45 degrees to the position shown in FIG. 8C in which passage 138 connects reaction chamber 30 to transducer 24. Transducer 24 senses the gas pressure in the reaction chamber (the pressure of the released carbon dioxide) and the resulting data is recorded (and/or displayed).

Controller 204 then operates stepper motor 90 to index valve shaft 90 degrees in the opposite direction (to return valve shaft 20 to the position of FIGS. 8A and 8D) in which valve passage 152 connects reaction chamber to line 190; and then operates stepper motor 76 to drive piston 40 to its uppermost position 42' to expel liquid from reaction chamber 30. Valve shaft 20 is next rotated to the FIG. 8E position in which the reaction chamber is connected to reagent line 186 and motor 76 then drives plunger 40 down to draw about one milliliter of lactic acid reagent into chamber 30. Valve shaft 20 is then indexed 90 degrees to the FIG. 8A position in which the reaction chamber is connected to the line 190 and transducer 24 is connected to the line 190 and transducer 24 is connected via vent passage 120 to atmosphere for equilibration. Plunger 40 is moved upwardly to eject reagent from reaction chamber 30 through line 190 into spin cup 194, and the spin cup is rotated at high speed by motor 196 to discharge the contents of cup 194 into waste chamber 202.

In this condition, the system has completed an analysis cycle and is ready for the next cycle with line 190 filled with reagent. The analysis cycle with this embodiment has a duration of about ½ minute, and the system measures total carbon dioxide content of serum specimens of about 30 microliters volume to a repeatability of about two percent.

While a particular embodiment of the invention has been show and described, various modifications will be apparent to those skilled in the art, and therefore it is not intended that the invention be limited to the disclosed embodiment or to details thereof and departures may be made therefrom within the spirit and scope of the invention.

What is claimed is:

1. A system for analyzing carbon dioxide content of a fluid comprising
   structure defining an inlet port,
   a reaction chamber,
   means to change the volume of said reaction chamber,
   a transducer for sensing a parameter of carbon dioxide in said reaction chamber,
   a flow control coupled between said chamber and said inlet port,
   said flow control having
   a first state in which said inlet port is connected to said reaction chamber, and
   a second state in which said reaction chamber is sealed,
   a chamber volume control for changing the volume of said reaction chamber, and
   a system controller for coordinately operating said flow control and said chamber volume control,
   said system controller having
   (1) a loading mode in which said flow control is operated to connect said reaction chamber to said inlet port and said volume control is then operated to increase the volume of said reaction chamber to draw sample and reagent through said inlet port structure into said chamber,
   (2) a degassing mode in which said flow control is operated to seal said reaction chamber and said volume control is then operated to further increase the volume of said reactin chamber after said flow control has sealed said reaction chamber to reduce the pressure in said chamber and facilitate release of carbon dioxide from said sample as a result of interaction of said reagent and said sample, and (3) a measuring mode in which said volume control is operated to decrease the volume of said reaction chamber to a predetermined value (of pressure or volume) and a parameter of the released carbon dioxide in said chamber is then measured by said transducer.

2. The system of claim 1 wherein said flow control includes a valve and a stepper motor type of valve controller, said reaction chamber includes a tube and a piston mounted for axial movement in said tube, and said volume control includes a stepper motor type of piston controller for moving said piston to change the volume of said reaction chamber.

3. A total carbon dioxide analyzer system comprising reaction chamber structure including a tube, a port in said tube, and a piston mounted for sliding movement in said tube to change the volume of said chamber between said port and said piston, a transducer for sensing a parameter of carbon dioxide in said reaction chamber, a valve coupled to said chamber, said valve having a sample inlet port, and a reagent inlet port, a valve control having a first state in which said sample inlet port is connected to said tube port, a second state in which said reagent inlet port is connected to said tube port, and a third state in which said tube port is closed so that said reaction chamber is sealed, and a piston control for moving said piston to vary the volume of said reaction chamber.

4. The system of claim 3 and further including a system controller for coordinately operating said valve control and said piston control, said controller having a reagent loading condition for storing reagent in said chamber, a sample loading condition for placing said valve in said first state and operating said piston control to increase the volume of said chamber to draw sample into said chamber for mixing with reagent in said chamber, a degassing condition for placing said valve in said third state and operating said piston control to increase the volume of said chamber to a volume larger than the chamber volume in said sample loading condition, and an analysis condition for operating said piston control to decrease the volume of said chamber to a volume less than the chamber volume in said degassing condition, and in which said transducer is connected to said chamber for sensing a parameter of carbon dioxide in said chamber.

5. The system of any one of claims 2-4 wherein said valve includes a housing, a seal member in said housing, and a movable valve member sealingly disposed in said seal member, and said seal member has a plurality of passages, one of said passages being a reagent inlet passage, a second of said passages being a sample inlet passage, and a third passage being connected to said chamber inlet.

6. The system of claim 3 and further including means for connecting a reagent reservoir to said reagent inlet port, a sample cup for receiving sample liquid to be analyzed, and a conduit of predetermined volume extending from said sample cup to said sample inlet port.

7. The system of either claim 1 or 3 and further including a stirring mechanism inside said reaction chamber, and an electromagnetic actuator outside said reaction chamber for operating said stirring mechanism to facilitate the reaction between the sample and the reactant and the release of gaseous carbon dioxide from the sample-reactant mixture in said reaction chamber.

8. The system of any one of claims 1-4 or 6 wherein said transducer includes a pressure sensor.

9. The system of either claim 2 or 3 wherein said valve includes a housing, a seal member in said housing, and a movable valve member sealingly disposed in said seal member, said transducer includes a pressure sensor mounted on said valve housing, and said seal member has a plurality of passages, one of said passages being a reagent inlet passage, a second of said passages being a sample inlet passage, a third passage being connected to said chamber inlet, and a fourth passage being connected to said pressure sensor.

10. The system of claim 9 and further including means for connecting a reagent reservoir to said reagent inlet passage, a sample cup for receiving sample liquid to be analyzed, and a conduit of predetermined volume extending from said sample cup to said sample inlet passage.

11. The system of claim 10 and further including a valve controller for moving said valve member, a piston controller for moving said piston to change the volume of said reaction chamber, and a sample cup controller for rotating said sample cup in a mixing action.

12. The system of claim 11 wherein said valve member is a rotatable valve shaft that has a plurality of through passages for interconnecting corresponding passages in said seal member as a function of the angular position of said valve shaft, each said through passage having a volume of less than twenty microliters, said seal member is a block of plastics material with a bore in which said valve shaft is press fitted, and a plurality of passages that extend from said bore, said housing member has a plurality of ports corresponding to and aligned with passages in said seal block, and said pressure sensor is secured to said housing member and seated against said seal member so that said pressure sensor is connected to said reaction chamber via a through passage of said shaft in one angular position of said valve shaft for measuring the carbon dioxide pressure in said reaction chamber.

13. The system of claim 12 and further including a system controller for coordinately operating said valve controller, said piston controller and said sample cup controller, said system controller having a reagent loading condition for storing reagent in said chamber, a sample loading condition for operating said valve controller to rotate said valve shaft to said first state and operating said piston controller to increase the volume of said chamber to draw sample from said sample cup through said conduit into said chamber for mixing with reagent in said chamber, a degassing condition for operating said valve controller to rotate said valve shaft to said third state and operating said piston controller to increase the volume of said chamber to a volume larger than the chamber volume in said sample loading condition to facilitate the release of carbon dioxide from the mixture in said chamber, and an analysis condition for operating said piston controller to decrease the volume of said chamber to a volume less than the chamber volume in said degassing condition and greater than the chamber volume in said reagent loading condition, and for operating said valve controller to rotate said valve shaft to connect said pressure sensor to said chamber for sensing the pressure of carbon dioxide in said chamber.

14. The system of claim 13 wherein said system controller further has a flush condition for operating said valve controller to rotate said valve shaft to said first state and operating said piston controller to decrease the volume of said chamber to force material from said reaction chamber through said conduit into said sample cup.

15. The system of claim 14 and further including stirring mechanism inside said reaction chamber, and an electromagnetic actuator outside said reaction chamber for operating said stirring mechanism when said system controller is in said degassing conditon to facilitate the release of gaseous carbon dioxide from the sample-reactant mixture in said reaction chamber.

* * * * *